US008870789B2

(12) United States Patent
Konya

(10) Patent No.: US 8,870,789 B2
(45) Date of Patent: Oct. 28, 2014

(54) LANCING SYSTEM AND TAPE CASSETTE FOR A LANCING DEVICE

(75) Inventor: Ahmet Konya, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 75 days.

(21) Appl. No.: 13/194,581

(22) Filed: Jul. 29, 2011

(65) Prior Publication Data

US 2012/0191011 A1    Jul. 26, 2012

Related U.S. Application Data

(63) Continuation of application No. PCT/EP2009/009340, filed on Dec. 31, 2009.

(51) Int. Cl.
*A61B 5/151* (2006.01)
*G01N 35/02* (2006.01)

(52) U.S. Cl.
CPC ................................. *A61B 5/15146* (2013.01)
USPC ........... 600/583; 600/575; 600/584; 606/181; 422/66; 436/44

(58) Field of Classification Search
USPC .................. 600/583, 584, 575; 606/181–183; 422/66; 436/44
See application file for complete search history.

(56) References Cited

U.S. PATENT DOCUMENTS

| 2003/0211619 | A1* | 11/2003 | Olson et al. ...................... 436/44 |
| 2005/0245845 | A1* | 11/2005 | Roe et al. ....................... 600/583 |
| 2007/0038150 | A1  | 2/2007  | Calasso et al. |
| 2007/0173740 | A1* | 7/2007  | Chan et al. .................... 600/583 |
| 2010/0292609 | A1  | 11/2010 | Zimmer et al. |

FOREIGN PATENT DOCUMENTS

| EP | 1360935 B1 | 12/2006 |
| EP | 1881332 A2 | 1/2008 |
| EP | 1690496 B1 | 11/2008 |
| EP | 1992284 A1 | 11/2008 |
| WO | 2005/107596 A2 | 11/2005 |
| WO | 2006/059241 A2 | 6/2006 |
| WO | 2007/077212 A2 | 7/2007 |

* cited by examiner

*Primary Examiner* — Max Hindenburg
*Assistant Examiner* — John Pani
(74) *Attorney, Agent, or Firm* — Roche Diagnostics Operations, Inc.

(57) ABSTRACT

A lancing system comprising a lancing elements carrier tape carrying a plurality of lancing elements, a tape transport unit for moving the lancing elements consecutively into a usage position by transporting the lancing elements carrier tape, a lancing drive for causing a lancing element located in the usage position to perform a lancing movement, and test elements with detection reagents for analyzing a body fluid sample obtained by a puncture is presented. Additionally, a test elements carrier tape is provided, which carries the test elements. The lancing elements carrier tape and the test element carrier tape are located on top of one another with tape sections that carry unused test elements or unused lancing elements.

17 Claims, 1 Drawing Sheet

LANCING SYSTEM AND TAPE CASSETTE FOR A LANCING DEVICE

CROSS-REFERENCE TO RELATED APPLICATIONS

This application is a continuation of PCT/EP2009/009340, filed Dec. 31, 2009, which is based on and claims priority to EP 09001459.8, filed Feb. 3, 2009, which is hereby incorporated by reference.

BACKGROUND

The present disclosure generally relates to a lancing system and, in particular, to a lancing system and a tape cassette for a corresponding lancing device.

A lancing system with a test element arranged on a carrier tape between lancing elements is known in the prior art. In this system, individual strips of film are glued onto the carrier tape, where the strips of film, each cover a lancing element and comprise a window. Before use, a lancing element must be displaced on the carrier tape so that the tip of the element is no longer covered by a strip of film. This requires a lancing device having complex mechanics. In addition, the film strips must be placed with the windows on the individual lancing elements with great precision leading to considerable manufacturing expenditure.

In addition, lancing systems are known in which test elements are designed integral with lancing elements. The disadvantage of such systems, however, is that sensitive detection reagents of the test element make sterilization of the lancing element difficult. Removing the sterile packaging from such a system also requires complex mechanics, because potentially remaining parts of the sterile packaging can impair sampling by partially covering a capillary channel or because interfering capillary effects may occur due to remaining film.

SUMMARY

According to the present disclosure, a lancing system is disclosed. The lancing system can comprise a lancing elements carrier tape carrying a plurality of lancing elements, a tape transport unit for moving the lancing elements consecutively into a usage position by transporting the lancing elements carrier tape, a lancing drive for causing a lancing element located in the usage position to perform a lancing movement, test elements for analyzing a body fluid sample obtained by a puncture and a test elements carrier tape, which carries the test elements. The lancing elements carrier tape and the test elements carrier tape can be located on top of one another with tape sections that carry unused test elements or unused lancing elements.

In accordance with one embodiment of the present disclosure, a tape cassette for a lancing device is also disclosed. The tape cassette can comprise a lancing elements carrier tape carrying a plurality of lancing elements and a test elements carrier tape carrying a plurality of test elements. The lancing elements carrier tape and the test elements carrier tape can be located on top of one another.

Accordingly, it is a feature of the embodiments of the present disclosure to provide a lancing system in a cost-effective manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

According to one exemplary embodiment, two different carrier tapes can be used. One carrier tape can be a lancing elements carrier tape, which carries the lancing elements, and the other carrier tape can be a test elements carrier tape, which carries the test elements. The two carrier tapes can be located on top of one another with tape sections that carry unused test elements or unused lancing elements. This structure can enable cost-effective manufacturing because lancing elements carrier tapes comprising lancing elements and test elements carrier tapes comprising test elements can be manufactured separately. For example, a lancing elements carrier tape comprising lancing elements and a test elements carrier tape carrying test elements can be placed on top of one another during production and can be subsequently folded in a zigzag manner so as to form a stack, or they can be wound to form a roll. In one embodiment, the test elements carrier tape can cover the unused lancing elements. In one exemplary embodiment, the test elements carrier tape can form a sterile packaging for the unused lancing elements.

According to another exemplary embodiment, the two carrier tapes can be located on top of one another with tape sections between which unused test elements and unused lancing elements can be located. In this way, both the lancing elements and the test elements can be protected from harmful environmental effects by the two carrier tapes and exposed by separating the two carrier tapes. It is also possible, for example, to arrange the test elements and the lancing elements in the same orientation on the two carrier tapes, so that only the lancing elements are covered, for example, by placing the test elements carrier tape on the lancing element carrier tape.

Figure 1:
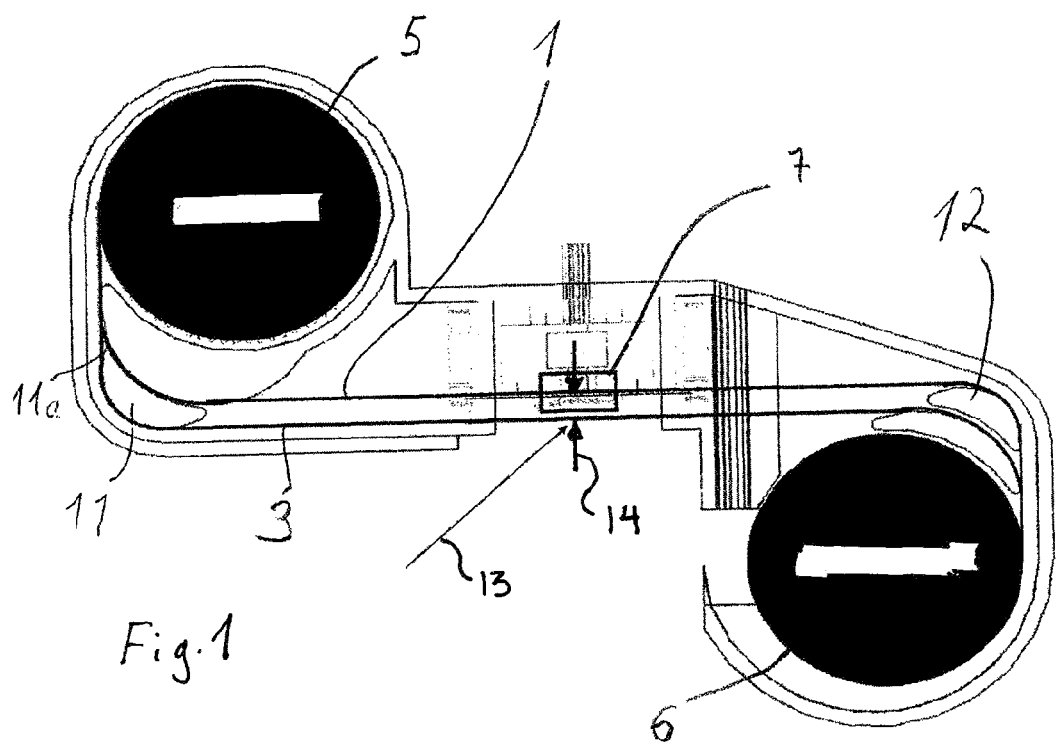
FIG. 1 illustrates a schematic illustration of a lancing system according to an embodiment of the present disclosure.

Referring initially to FIG. 1, the lancing system can comprise a lancing elements carrier tape 1 carrying lancing elements 2 and a test elements carrier tape 3 carrying test elements 4 with detection reagents for analyzing a body fluid sample obtained by a puncture. In one embodiment, the test elements carrier tape 3 and the lancing elements carrier tape 1 can be wound on top of one another onto a reel 5 in a supply chamber. In another embodiment, the test elements carrier tape 3 and the lancing elements carrier tape 1 can also be folded into a stack, for example.

Using a tape transport unit, shown as a winding unit 6 in FIG. 1, the test elements carrier tape 3 and the lancing elements carrier tape 1 can be transported and the lancing elements 2 can be consecutively moved into a usage position, in which they can perform a lancing movement by a lancing drive 7. In an exemplary embodiment, the lancing movement can be substantially perpendicular to the drawing plane of FIG. 1 as illustrated by arrow 13.

In an exemplary embodiment, the lancing system can comprises a first tape guide 11. The first tape guide 11 can separate the test elements carrier tape 3 from the lancing elements carrier tape 1 and can guide the test elements carrier tape 3 from the lancing elements carrier tape 1 on different paths spaced from one another. The first tape guide 11, causing the separation of the test elements carrier tape 3 and the lancing elements carrier tape 1, can be positioned between the test elements carrier tape 3 and the lancing elements carrier tape 1. The first tape guide 11 can, for example, have a wedge-shaped front 11a onto which the test elements carrier tape 3 and the lancing elements carrier tape 1 still connected can be moved during the tape transport.

So as to guide the test elements carrier tape 3 and the lancing elements carrier tape 1 that are spaced from one another after separation, the first tape guide 11 can have a curved design. The test elements carrier tape 3 and the lancing elements carrier tape 1 can be guided on different paths. The different paths of the test elements carrier tape 3 and of the lancing elements carrier tape 1 can comprise at least one curved path section, respectively, wherein the curved path section of the test elements carrier tape 3 and the curved path section of the lancing elements carrier tape 1 can run side by side and the two curved path sections can be curved in the same direction.

As illustrated in FIG. 1, the test elements carrier tape 3 and the lancing elements carrier tape 1 can be bent and guided along a curve. Behind the usage position of the lancing elements 2, the test elements carrier tape 3 and the lancing elements carrier tape 1 can be joined again and can be wound on top of each other on the winding unit 6. A second tape guide 12, which can be likewise disposed between the test elements carrier tape 3 and the lancing elements carrier tape 1, can be provided for joining the test elements carrier tape 3 and the lancing elements carrier tape 1. The second tape guide 12 can be curved in the opposite direction as the first tape guide 11.

The spacing at which the test elements carrier tape 3 and the lancing elements carrier tape 1 can be guided between the first and second tape guide 11, 12 can be large enough so that a gap that can be formed between the test elements carrier tape 3 and the lancing elements carrier tape 1 causes no capillary forces on a body fluid sample taken up by a test element 4. In one embodiment, the test elements carrier tape 3 and the lancing elements carrier tape 1 can be guided parallel to one another spaced apart at least approximately 2 mm. In another embodiment, the test elements carrier tape 3 and the lancing elements carrier tape 1 can be spaced apart at least approximately 5 mm. In this way, an offset between the lancing elements and the test elements can be compensated for so that the test element 4 can reach a lancing element for transferring a sample.

Figure 2:
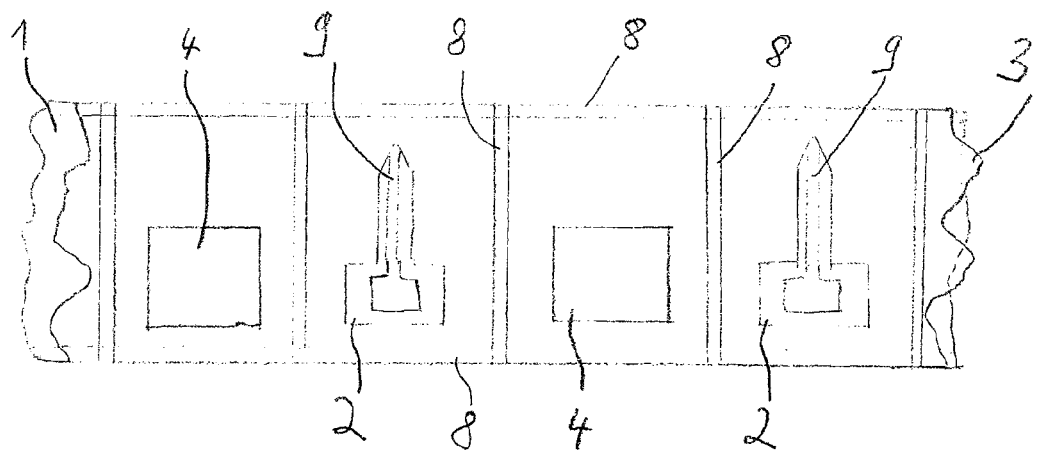
FIG. 2 illustrates a schematic illustration of a lancing elements carrier tape comprising unused lancing elements and a test elements carrier tape glued thereto, which comprises unused test elements according to an embodiment of the present disclosure.

FIG. 2 illustrates, by way of example, tape sections of the test elements carrier tape 3 and the lancing elements carrier tape 1 that can be located on top of one another, comprising unused test elements 4 and unused lancing elements 2. As viewed in the tape direction, the test elements 4 can be located between the lancing elements 2, respectively, which is to say the test elements carrier tape 3 and the lancing elements carrier tape 1 can be located with offset on top of one another. In one embodiment, the spacing between the unused lancing elements 2 and the unused test elements can agree with the spacing at which the test elements carrier tape 3 and the lancing elements carrier tape 1 are guided after separation, for example between the first and second tape guides 11, 12.

The test elements carrier tape 3 can cover the unused lancing elements 2. The test elements carrier tape 3 and the lancing elements carrier tape 1 can adhere to one another with tape sections between which the unused test elements 4 and the unused lancing elements 2 can be located. One embodiment of the adhesive surfaces 8 surrounding the lancing elements 2 and the test elements 4 is illustrated in FIG. 2.

The unused lancing elements 2 can be disposed in chambers, the upper faces of which can be formed by the test elements carrier tape 3 and the lower faces of which can be formed by the lancing elements carrier tape 1. The lancing elements 2 can thus be packaged in a sterile manner with low expenditure. The chambers can be automatically opened by separating the test elements carrier tape 3 and the lancing elements carrier tape 1 so that the lancing elements 2 can be ready for use when they reach their usage position. In one embodiment, the test elements carrier tape 3 and the lancing elements carrier tape 1 can be detachably glued to one another on release paper, similar to adhesive labels, so that the test elements carrier tape 3 and the lancing elements carrier tape 1 can be easily separated from one another. One embodiment of the adhesive surfaces 8 of the test elements carrier tape 3 and the lancing elements carrier tape 1 enclosing the lancing elements 2 and the test elements 4 is illustrated in FIG. 2.

In one embodiment, the lancing elements carrier tape 1 can cover the unused test elements 4. In this way, the test elements 4 can be protected from harmful environment effects without additional expenditure. Similarly to the lancing elements 2, the test elements 4 can be disposed in chambers, which can be formed by the test elements carrier tape 3 and the lancing elements carrier tape 1 adhering to one another.

Because of the first tape guide 11, illustrated in FIG. 1, which guides the test elements carrier tape 3 and the lancing elements carrier tape 1 on different paths, a test element 4 can be moved to a lancing element 2 to take up a body fluid sample. The test elements 4 and the lancing elements 2 can travel distances having differing lengths from the point at which the test elements carrier tape 3 and the lancing elements carrier tape 1 are separated from one another until a sample can be transferred from a lancing element 2 onto a test element 4. The distances differ by the spacing between test elements 4 and lancing elements 2 before the test elements carrier tape 3 and the lancing elements carrier tape 1 are separated, this spacing can be measured in the tape direction. The differently long distances can thus compensate for an offset between the lancing elements carrier tape 1 and the test elements carrier tape 3.

In one embodiment, the differently long distances can be caused by guiding the test elements carrier tape 3 and the lancing elements carrier tape 1 along a curve after separation. In this way, the distance resulting for the carrier tape guided on the inside of the curve in the curvature direction, which in FIG. 1 is the lancing elements carrier tape 1, can be shorter than that resulting for the carrier tape guided on the outside of the curvature direction, which in FIG. 1 is the test elements carrier tape 3.

It does not matter, per se, which one of the test elements carrier tape 3 and the lancing elements carrier tape 1 is guided on the inside and which one is guided on the outside. With the differing paths, it can always be possible to guide a test element 4 for sampling to a lancing element 2. In one embodiment, because of the differing paths, a test element 4 can be positioned over the lancing element 2, which can be located in the usage position, for example in a receptacle of the lancing drive 7. In this way, during puncture, a lancing element 2 can take up a body fluid sample with the sample receiving unit 9 thereof, for example a capillary channel, and then can transfer this sample to test element 4. In one embodiment, during a puncture, only the lancing element 2 and the lancing elements carrier tape 1, but not the test elements carrier tape 3, can be moved. To transfer the sample, a movement, indicated by reference numeral 14 in FIG. 1, of the lancing element, or of the test element, substantially perpendicular to the puncture direction can be carried out. For example, the lancing drive 7 can push the lancing elements carrier tape 1 against the test elements carrier tape 3 after, or during, a puncture. In one embodiment, the lancing element 2 can remain connected to the lancing elements carrier tape 1 during a puncture. After taking up a sample, the test element can press against a measuring unit. In one embodiment, the measuring unit can be an optical measuring unit. In one exemplary embodiment, the measuring unit can be a CMOS sensor, for example.

In one embodiment, a test element 4 can take up a body fluid sample from a lancing element 2 that is located in the usage position. However, in principle, it can also be possible to transfer the sample at another location such as, for example, to transport the test elements carrier tape 3 and the lancing elements carrier tape 1 a bit further after a puncture before bringing a test element 4 in contact with the sample receiving unit 9 of a lancing element 2. For example, additional tape guides may be provided, which together can form a gap through which the test elements carrier tape 3 and the lancing elements carrier tape 1 can be guided, so that a lancing element 2 and a test element 4 can come in contact with one another.

Behind the usage position, the lancing elements carrier tape 1 and the test elements carrier tape 3 can be joined again. To this end, the test elements carrier tape 3 and the lancing elements carrier tape 1 can be guided so that the previously differently long distances can be compensated for again, which is to say, the original arrangement of the test elements 4 between the lancing elements 2 can be re-established. This can be achieved, in one embodiment, by guiding the test elements carrier tape 3 and the lancing elements carrier tape 1 behind the usage position with spacing along a curve that can be curved oppositely to the preceding curve, which is to say the second tape guide 12 can be curved oppositely from the first tape guide 11. In this way, the test elements carrier tape 3 and the lancing elements carrier tape 1 can be wound with tape sections carrying used test elements 4 or lancing element 2 onto one another without difficulty using the winding unit 6. In one embodiment, the winding unit 6 can wind the test elements carrier tape 3 and the lancing elements carrier tape 1 in a winding direction that can be opposite of the winding direction in which the test elements carrier tape 3 and the lancing elements carrier tape 1 are wound with tape sections carrying unused test elements 4 or unused lancing elements 2. However, it can also be possible to position the reel 5 and the winding unit 6 minor-symmetrically in relation to one another, as is the case in conventional audio tape cassettes.

As explained above, in the embodiment illustrated in FIG. 2, prior to separating the test elements carrier tape 3 from the lancing elements carrier tape 1, the test elements 4 can be located between the lancing elements 2, respectively, as viewed in the tape direction. However, in principle, it can also be possible to position the test elements carrier tape 3 and the lancing elements carrier tape 1 on top of one another so that unused lancing elements 2 and unused test elements 4 can be positioned on top of one another, and consequently, no offset between the lancing elements 2 and test elements 4 needs to be compensated for by the tape guide. For example, the test elements carrier tape 3 and the lancing elements carrier tape 1 can be guided together and not be separated until just before the usage position by a separating element disposed in between them such as, for example, by a pin, past which they can be guided symmetrically on different sides.

In another embodiment, the lancing system can comprises a hand device and a tape cassette, which can be inserted in the lancing device. The tape cassette can contain the lancing elements carrier tape carrying a plurality of lancing elements and a test elements carrier tape carrying a plurality of test elements. The lancing elements carrier tape and the test elements carrier tape can be located on top of one another such as, for example, they can be wound on top of one another or can form a stack folded in a zigzag manner. It can also be possible, however, to have a lancing device with no tape replacement. Such a hand device can be discarded as a disposable device as soon as the supply of lancing elements and test elements contained therein is used up.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A lancing system, the lancing system comprising:
a lancing elements carrier tape carrying a plurality of lancing elements;
a tape transport unit for moving the lancing elements consecutively into a usage position by transporting the lancing elements carrier tape;
a lancing drive for causing a lancing element located in the usage position to perform a lancing movement;
test elements for analyzing a body fluid sample obtained by a puncture; and
a test elements carrier tape, which carries the test elements, wherein the lancing elements carrier tape and the test elements carrier tape are located on top of one another in a face to face arrangement with tape sections that carry unused test elements or unused lancing elements and wherein unused lancing elements are positioned between the test elements carrier tape and the lancing elements carrier tape which are joined together along a chamber perimeter surrounding each unused lancing element whereby each unused lancet is fully enclosed in a chamber having one face formed by the test elements carrier tape and an opposing face formed by the lancing elements carrier tape wherein when a section of the lancing elements carrier tape is separated from a section of the test elements carrier tape the separated section of the lancing elements carrier tape carries only lancing elements and the separated section of the test elements carrier tape carries only test elements.

2. The lancing system according to claim 1, wherein the test elements have detection reagents.

3. The lancing system according to claim 1, wherein the test elements carrier tape covers the unused lancing elements.

4. The lancing system according to claim 1, wherein the lancing elements carrier tape covers the unused test elements.

5. The lancing system according to claim 1, wherein sections of the test elements carrier tape and the lancing elements carrier tape carrying unused test elements and unused lancing elements are adhered to one another.

6. The lancing system according to claim 1, wherein the lancing elements comprise a sample receiving unit.

7. The lancing system according to claim 1, wherein the lancing elements and the test elements are moved toward one another perpendicular to the puncture direction to transfer a sample from a lancing element to a test element.

8. The lancing system according to claim 1, further comprises, a tape guide that separates the test elements carrier tape from the lancing elements carrier tape and that guides the test elements carrier tape and the lancing elements carrier tape on different paths.

9. The lancing system according to claim 8, wherein the different paths of the test elements carrier tape and of the lancing elements carrier tape each comprise at least one curved path section, wherein the at least one curved path section of the test elements carrier tape and the at least one curved path section of the lancing elements carrier tape run side by side spaced from one another and curved in the same direction.

10. The lancing system according to claim 9, wherein the test elements are located between the lancing elements, as viewed in a lengthwise direction of the tapes, prior to separating the test elements carrier tape from the lancing elements carrier tape.

11. The lancing system according to claim 8, wherein the different paths guide the test elements and the lancing elements from a point at which the test elements carrier tape and the lancing elements carrier tape are separated from one another to a position where a sample is transferred from a lancing element onto a test element.

12. The lancing system according to claim 8, wherein the tape guide is disposed between the lancing elements carrier tape and the test elements carrier tape.

13. The lancing system according to claim 8, wherein test elements and lancing elements travel distances having differing lengths from a point at which the test elements carrier tape and the lancing elements carrier tape are separated from one another to a position where a sample is transferred from a lancing element onto a test element.

14. The lancing system according to claim 8, wherein the tape guide includes first and second tape guides and wherein, in a travel direction of the tapes, the first tape guide bends the test elements carrier tape and the lancing element carrier tape in a first bending direction before the usage position and, at a location following the usage position, the second tape guide bends the lancing elements carrier tape in a second bending direction opposite the first bending direction.

15. The lancing system according to claim 1, wherein before usage of one of the lancing elements and one of the test elements, the lancing elements carrier tape and the test elements carrier tape carrying the one lancing element and the one test element are separated from each other and following usage of the one lancing element and the one test element, the lancing elements carrier tape and the test elements carrier tape carrying the one lancing element and the one test element are joined and wound with the lancing element carrier tape and the test element carrying tape on top of one another.

16. A tape cassette for a lancing device, the tape cassette comprising:
a lancing elements carrier tape carrying a plurality of lancing elements; and
a test elements carrier tape carrying a plurality of test elements, wherein the lancing elements carrier tape and the test elements carrier tape are located on top of one another in a face to face arrangement and wherein unused lancing elements are positioned between the test elements carrier tape and the lancing elements carrier tape which are joined together along a chamber perimeter surrounding each unused lancing element whereby each unused lancet is fully enclosed in a chamber having one face formed by the test elements carrier tape and an opposing face formed by the lancing elements carrier tape and wherein, after separation of a section of the lancing elements carrier tape from a section of the test elements carrier tape the separated section of the lancing elements carrier tape carries only lancing elements and the separated section of the test elements carrier tape carries only test elements.

17. A lancing system, the lancing system comprising:
a lancing elements carrier tape carrying a plurality of lancing elements;
a tape transport unit for moving the lancing elements consecutively into a usage position by transporting the lancing elements carrier tape in a travel direction;
a lancing drive for causing a lancing element located in the usage position to perform a lancing movement;
test elements for analyzing a body fluid sample obtained by a puncture;
a test elements carrier tape, which carries the test elements, wherein the lancing elements carrier tape and the test elements carrier tape are located on top of one another with tape sections that carry unused test elements or unused lancing elements;
a tape guide disposed before the usage position in the travel direction and between the lancing elements carrier tape and the test elements carrier tape wherein the tape guide separates the test elements carrier tape from the lancing elements carrier tape and guides the test elements carrier tape and the lancing elements carrier tape on paths of different lengths from a point at which the test elements carrier tape is separated from the lancing elements carrier tape to a second point at which a sample is transferred from one of the lancing elements to one of the test elements; and
wherein the test elements are located between the lancing elements, as viewed in a lengthwise direction of the tapes, prior to separating the test elements carrier tape from the lancing elements carrier tape.

* * * * *